(12) United States Patent
Swales

(10) Patent No.: US 10,350,317 B2
(45) Date of Patent: Jul. 16, 2019

(54) APPARATUS AND METHOD FOR SEALING ZONES OR ROOMS

(71) Applicant: GETINGE STERILIZATION AB, Getinge (SE)

(72) Inventor: Tim Swales, Viken (SE)

(73) Assignee: GETINGE STERILIZATION AB, Getinge (SE)

( * ) Notice: Subject to any disclaimer, the term of this patent is extended or adjusted under 35 U.S.C. 154(b) by 74 days.

(21) Appl. No.: 15/113,220

(22) PCT Filed: Jan. 9, 2015

(86) PCT No.: PCT/GB2015/050032
§ 371 (c)(1),
(2) Date: Jul. 21, 2016

(87) PCT Pub. No.: WO2015/110790
PCT Pub. Date: Jul. 30, 2015

(65) Prior Publication Data
US 2017/0007730 A1    Jan. 12, 2017

(30) Foreign Application Priority Data

Jan. 24, 2014    (GB) .................................. 1401201.7

(51) Int. Cl.
*A61L 2/07*    (2006.01)

(52) U.S. Cl.
CPC ........... *A61L 2/07* (2013.01); *A61L 2202/121* (2013.01); *A61L 2202/122* (2013.01); *A61L 2202/14* (2013.01)

(58) Field of Classification Search
CPC ..... A61L 2/07; A61L 2/24; A61L 2/26; A61L 2202/121; A61L 2202/122; A61L 2202/14; B65D 90/50; B65D 90/501; B65D 90/503; B65D 90/505; B65D 90/506
See application file for complete search history.

(56) References Cited

U.S. PATENT DOCUMENTS

| | | | |
|---|---|---|---|
| 4,466,552 A | 8/1984 | Butterworth | |
| 6,758,970 B1 | 7/2004 | Nurminen et al. | |
| 2004/0265167 A1* | 12/2004 | Morrison | A61L 2/14 422/33 |

FOREIGN PATENT DOCUMENTS

| | | |
|---|---|---|
| CN | 101698108 A | 4/2010 |
| CN | 202115871 U | 1/2012 |
| EP | 1 787 662 A1 | 5/2007 |

(Continued)

OTHER PUBLICATIONS

Translation of CN 202115871, China, Jan. 18, 2012, Xiaotao Liu.*

(Continued)

*Primary Examiner* — George R Koch

(57) ABSTRACT

A seal arrangement for sealing a space between a sterilization unit and adjacent walls in order to separate first and second rooms has a double seal gasket arrangement with a seal chamber there within. The seal chamber may be pressurized with a fluid and then the pressure within the seal chamber monitored by a pressure sensor. The double seal assembly provides an arrangement which can give an indication of the quality of the seal in order to detect any leakage and a more secure seal around the sterilization unit and as a result secure separation between a sterile or contaminated room and a general hospital area.

20 Claims, 8 Drawing Sheets

(56) References Cited

FOREIGN PATENT DOCUMENTS

| | | |
|---|---|---|
| WO | WO 2007/000639 A1 | 1/2007 |
| WO | WO 2007/113660 A2 | 10/2007 |
| WO | WO 2013/185831 A1 | 12/2013 |

OTHER PUBLICATIONS

Translation of CN 101598108, China, Apr. 28, 2010, Jinhe Chen.*
International Search Report (PCT/ISA/210) dated May 15, 2015, by the European Patent Office as the International Searching Authority for International Application No. PCT/GB2015/050032.
Written Opinion (PCT/ISA/237) dated May 15, 2015, by the European Patent Office as the International Searching Authority for International Application No. PCT/GB2015/050032.

* cited by examiner

B-B
NOT TO SCALE

APPARATUS AND METHOD FOR SEALING ZONES OR ROOMS

This application is a 371 of PCT/GB2015/050032, filing date Jan. 9, 2015.

TECHNICAL FIELD

The present invention relates to apparatus and a method for sealing zones or rooms, particularly in a medical environment, for instance to keep a zone or room sterilized or to isolate a contaminated area.

BACKGROUND ART

There are many instances, particularly in a hospital environment, in which it is necessary to seal an area or room for medical purposes. For instance, some rooms must be kept highly sterilized and thus separate from the general hospital areas, while in other instances a contamination zone needs to be kept sealed. A transition between such zones, that is from a sterile or contaminated zone to a general area, normally provides for sterilization. For this purpose it is common to locate between the two rooms a sterilization unit, for instance an autoclave, which provides the entry and exit points between the rooms. Passage from one room to another must therefore be through the sterilization unit.

In practice, an autoclave or other sterilization unit is fitted in an aperture of a wall between the two rooms and sealed to the walls by a sealing device, commonly a gasket or the like. The autoclave includes doors at either side, each leading to a respective room.

A problem occurs with conventional arrangements in that it is difficult to verify the quality of the seals between the autoclave and the walls and thus whether there may be any leakage which compromises the cleanliness or containment.

SUMMARY OF THE INVENTION

The present invention seeks to provide an improved apparatus and method of sealing zones or rooms, particularly in a medical environment.

According to an aspect of the present invention, there is provided apparatus for sealing first and second zones from one another including: a sterilization unit disposable in a structure separating the first and second zones, the sterilization unit including a chamber and providing therethrough access to the first and second zones; a sealing unit disposed around at least a part of the sterilization unit, wherein the sealing unit includes first and second seal elements each providing a seal between the sterilization unit and the separating structure; filler material disposed between the first and second seal elements, wherein the filler material provides a measurable characteristic; and at least one sensor disposed to measure said measurable characteristic.

The structure provides a sealing arrangement with a measurable indication of the quality of the seal achieved. Specifically, any leakage in the seals can be detected by a change in the measurable characteristic. Moreover, the use of two sealing elements provides a more secure seal, specifically for the sealing function to be maintained even when it is detected that there is a sealing element defect. Typically, any defects will not occur simultaneously in the two sealing elements, so that overall sealing will be maintained by non-compromised the sealing element even when it is detected that there is a sealing defect. The filler advantageously also provides a sealing function, thereby enhancing the overall effectiveness of the seal.

Preferably, the first and second seal elements are spaced from one another, the filler material being disposed in said space.

The filler material is advantageously a fluid, for example a liquid or a gas.

In a preferred embodiment the measurable characteristic is pressure. It is to be understood, however, that other characteristics could be measured, such as colour, chemical constitution of the filler etc.

In the preferred embodiment, the filler is of a nature able to escape from either of the seal elements when an incomplete seal between the sterilization chamber and adjacent structure occurs.

In a practical embodiment, the apparatus includes a fitting element attachable to an adjacent structure and providing a support for the first and second seal elements. In other words, the apparatus includes the elements to be attached to a support structure to provide a solid sealed coupling thereto and the seals to the sterilization chamber.

Typically, the sterilization chamber includes first and second doors for access therethrough.

According to another aspect of the present invention, there is provided a method of sealing first and second zones from one another including the steps of: disposing a sterilization unit between said first and second zones and facing an adjacent structure, the sterilization unit providing therethrough access to the first and second zones; disposing a sealing unit around at least a part of the sterilization chamber, the sealing unit including first and second seal elements each providing a seal between the sterilization chamber and an adjacent structure; disposing filler material between the first and second seal elements; sensing for a change in at least one parameter of the filler unit over time and therefrom determining the quality of sealing.

Other features and advantages will be apparent form the following description of preferred embodiments.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

It is to be understood that the accompanying drawings are schematic only and focus upon the salient elements of the apparatus taught herein. Elements of the apparatus and system which are not necessary from the understanding of the teachings herein have been omitted for the sake of clarity. It is also to be understood that the drawings are not intended to show any of the components to scale.

Figure 1:
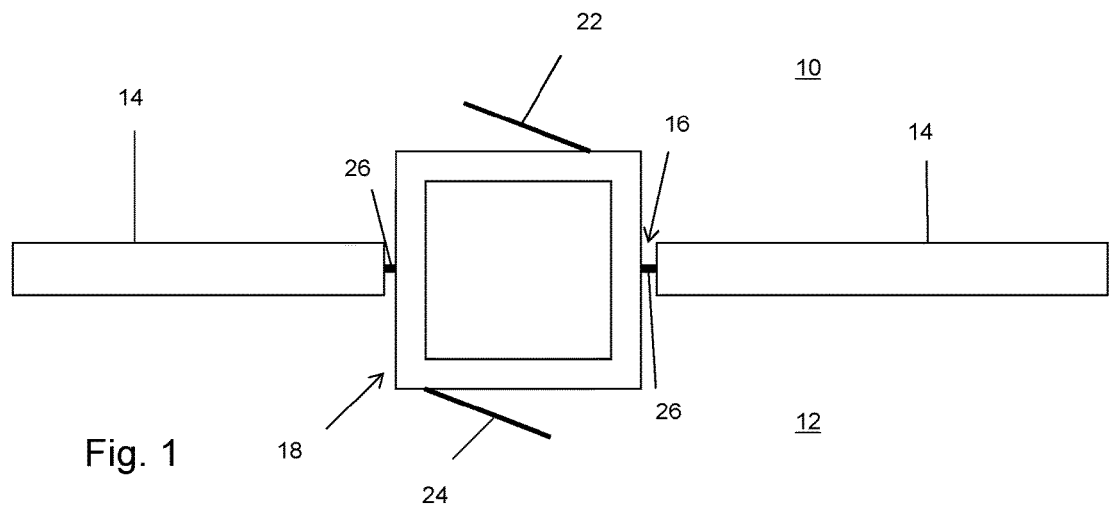
FIG. 1 is a schematic diagram showing the basic arrangement of a sealed room.

Referring first to FIG. 1, this shows in schematic form the general arrangement for zone or room isolation. The arrangement separates two rooms or zones 10, 12 from one another, which in this example are delineated by a dividing wall 14 having an opening 16 therein. Disposed across the dividing wall 14 within the opening 16 is a sterilization unit 18, typically an autoclave, in this example a steam sterilizer. The sterilization unit 18 includes a sterilization chamber 20 and opposing doors 22, 24 for access into the chamber 20 and between the rooms or zones 10, 12. A sealing assembly 26 is disposed around the exterior of the sterilization unit 18 to seal any space or gap between the opening 16 and the sterilization unit 18. Access between the two rooms or zones 10, 12 can be achieved solely through the sterilization chamber 20, thereby maintaining one of the zones under sterile conditions or containing securely contaminants within one of the zones.

Figure 2:
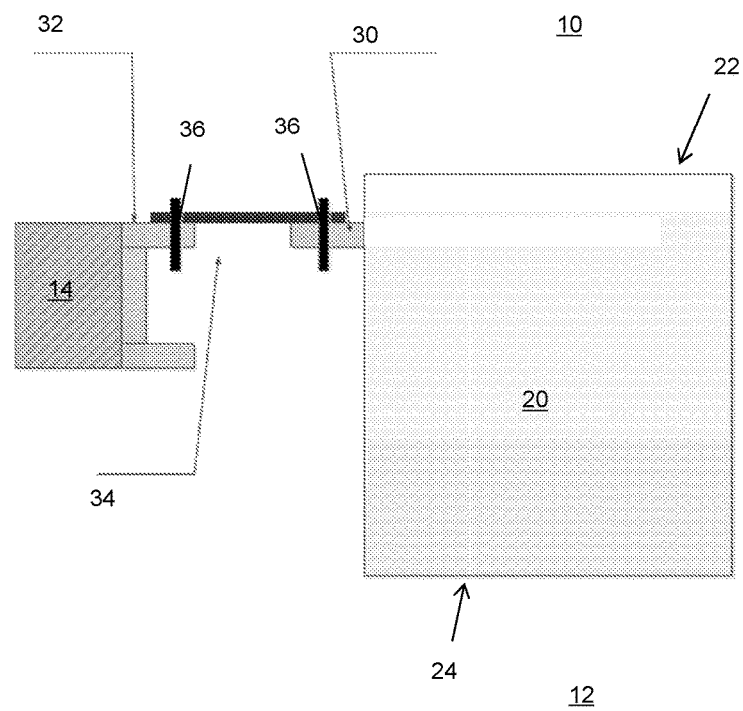
FIG. 2 is a schematic diagram illustrating the structure of a conventional sealing arrangement.

An example of seal assembly for the structure of FIG. 1 can be seen in FIG. 2. Shown schematically in this drawing is a sterilization-side flange 30, which may be formed integrally with the sterilization unit 18 and which extends around the outside perimeter of the unit 18, both at its sides and also along the top and bottom walls of the unit 18. Attached to the walls 14, and equally to a ceiling or wall structure above the sterilization unit 18 and along the floor, there this a frame element 32. Connected across the flange 30 and frame element 32 is a sealing unit 34, coupled in this example by a series of bolts 36 disposed at spaced intervals along the sealing unit 34 and fitting into appropriate holes in the flange 30 and frame 32. All gaps between the walls and the sterilization unit 18 and the adjacent structure or structures, in this example walls 14, are typically sealed in this manner. The intention of this arrangement, as the person skilled in the art will know, is to ensure that the only path from zone 10 to zone 12 and vice versa is through the sterilization unit 18.

A variety of methods are known for testing the integrity of a seal of the type shown in FIG. 2. One method commonly used is to pressurise one room 10 relative to the other room 12 and then to check for leaks using sensors in room 10. However, such testing has shortcomings. One occurs because the pressurisation of, for example, room 10 can only be carried out once all penetrations and apertures in the room 10 have been closed, usually sometime after installation of the sterilization unit 18. Furthermore, such testing is a "one time" event, carried out during the construction of the building. After commissioning, leakages can result in the escape of pathogens from one room when used for containment or contamination of a sterile room. In particular, the problem with the arrangement shown in FIG. 2 is that there is no way of determining whether the sealing element 34 provides a secure seal between the two rooms or zones 10, 12. Any leakage from the sealing element 34 cannot generally be detected.

Figure 3:
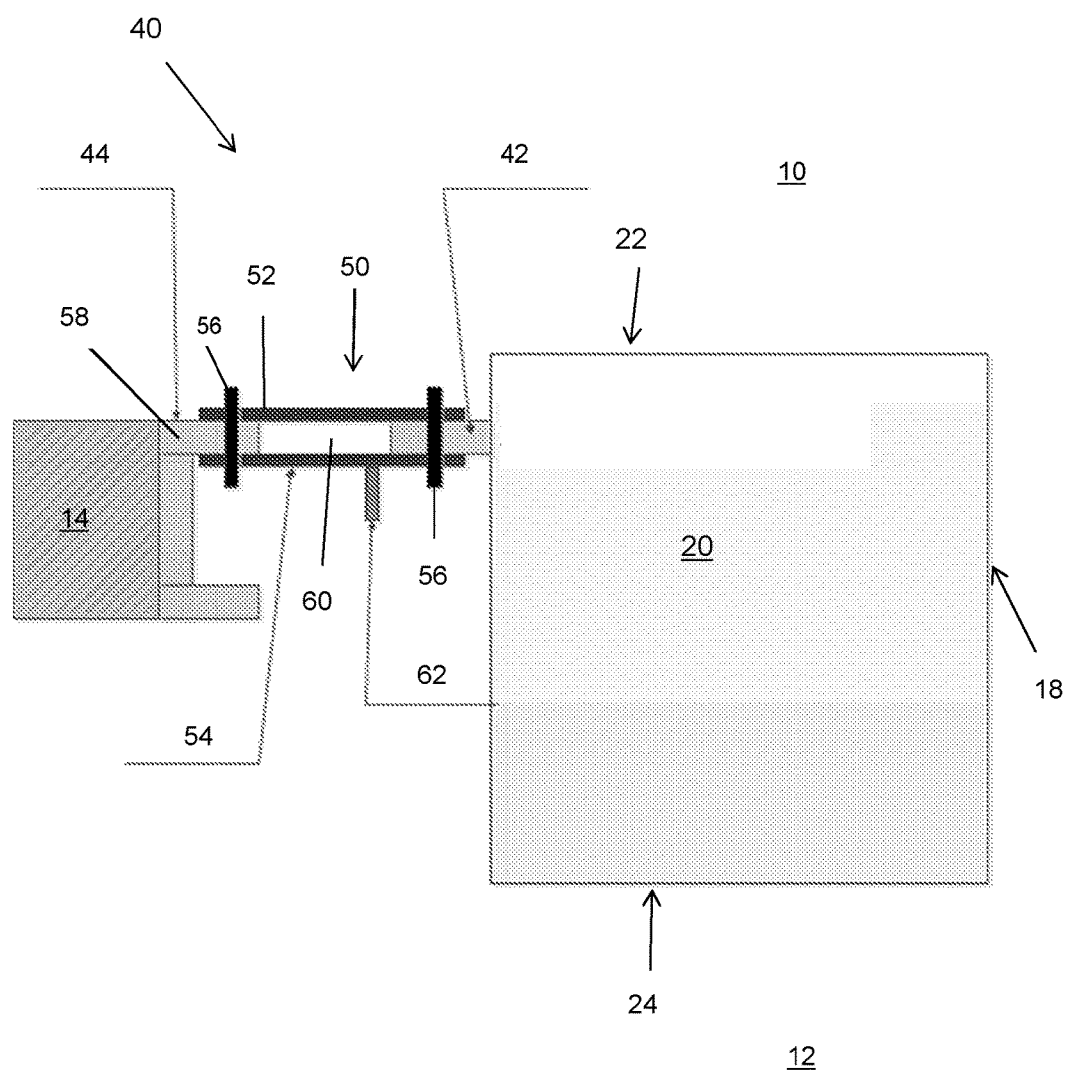
FIG. 3 is a schematic diagram illustrating the structure of a preferred embodiment of sealing arrangement as taught herein.

Referring now to FIG. 3, this shows in schematic form a preferred embodiment of the present invention. Disposed between the sterilization unit 18 and the wall 14 is a seal assembly 40 which includes a sterilizer-side flange 42 extending along the sides of the sterilization unit 18 which are disposed in the opening 16 in wall 14. The seal assembly 14 also includes a wall frame element 44, which is preferably a metal fabrication installed within the wall aperture where the sterilizer unit 18 is to be located. The metal frame 44 is sealed to the adjacent walls, ceiling and floor, advantageously during building construction. The connection to the walls, floor and ceiling is airtight.

The embodiment of FIG. 3 includes a double seal assembly 50, which includes first and second seal strips or gaskets 52, 54 disposed either side of the flange 42 and of a flange 58 of the wall frame 44, leaving a gap or seal chamber 60 between the first and second gaskets 52, 54. The gaskets 52, 54 are fixed to the flange 42 and wall frame 44 by any suitable means, in this example by a series of bolts 56. Any other coupling or bonding arrangement may be used in place of the bolts 56.

The gaskets 52, 54 may be made of a rubberised material, for instance ethylenepropylenediene monomer (M-class) rubber (EPDM), or any other suitable sealing material. In another embodiment the gaskets could be made of sheet metal, for instance, with rubberised seals disposed around their peripheries. The gaskets could each be made of the same material but it is not excluded that they may be made of different materials.

Coupled to the double seal assembly 50, in this example through an opening or port in one of the gaskets 54, is a sensor probe 62, preferably a pressure sensor. When the double seal arrangement 50 is assembled as shown, with the gaskets 52, 54 fitted and sealed to the flange 42 and wall frame 44 as shown, the seal chamber 60 between the gaskets 52, 54 can be pressurised with a suitable fluid (air may be used as one example). Pressurisation could usefully be by pumping fluid under pressure through the same aperture or port into which the pressure sensor 62 is then fitted, although this could be by any other suitable means or inlet port.

As long as the gaskets 52, 54 provide a proper seal, there should be no drop in pressure of fluid held in the seal chamber 60. On the other hand, where there is leakage through or around either of the gaskets 52, 54, pressure in the seal chamber 60 will drop, which will be detected by the pressure sensor 62. In practice, the sensor probe 62 will be coupled to a suitable control or warning unit (not shown) which will generate a warning signal indicative of seal failure. A warning unit could be coupled directly to the assembly or could be a remote monitoring unit, in which case a communication link, wired or wireless, may be provided.

It will be appreciated that the assembly shown can determine the quality of seal provided by the double seal assembly 50 even before completion of construction of the building, that is before any other apertures or penetrations in the wall 14 or elsewhere in the room 10/12 have been sealed. Furthermore, provision of dual seal gaskets 54, 56 provides added security in that detection of a leak is likely to occur when just one of the two gaskets 52, 54 is defective, thereby without loss of sterilization or containment in the associated room 10/12.

It is to be understood that the seal chamber 60 may be provided with other detectable fluids, one example being a pure gas, with an appropriate gas sensor able to detect the purity (concentration) of that gas within the seal chamber 60. Another example provides a coloured fluid. In practice the seal chamber 60 may be filled with any suitable fluid which provides a detectable parameter. In other embodiments the seal chamber 60 may be held under vacuum, with the pressure sensor 62 measuring for loss of vacuum, that is pressure rise, over time.

Referring now to FIGS. 4 to 9, these show features of a practical embodiment of sterilization unit and double seal assembly as taught herein.

Figure 4:
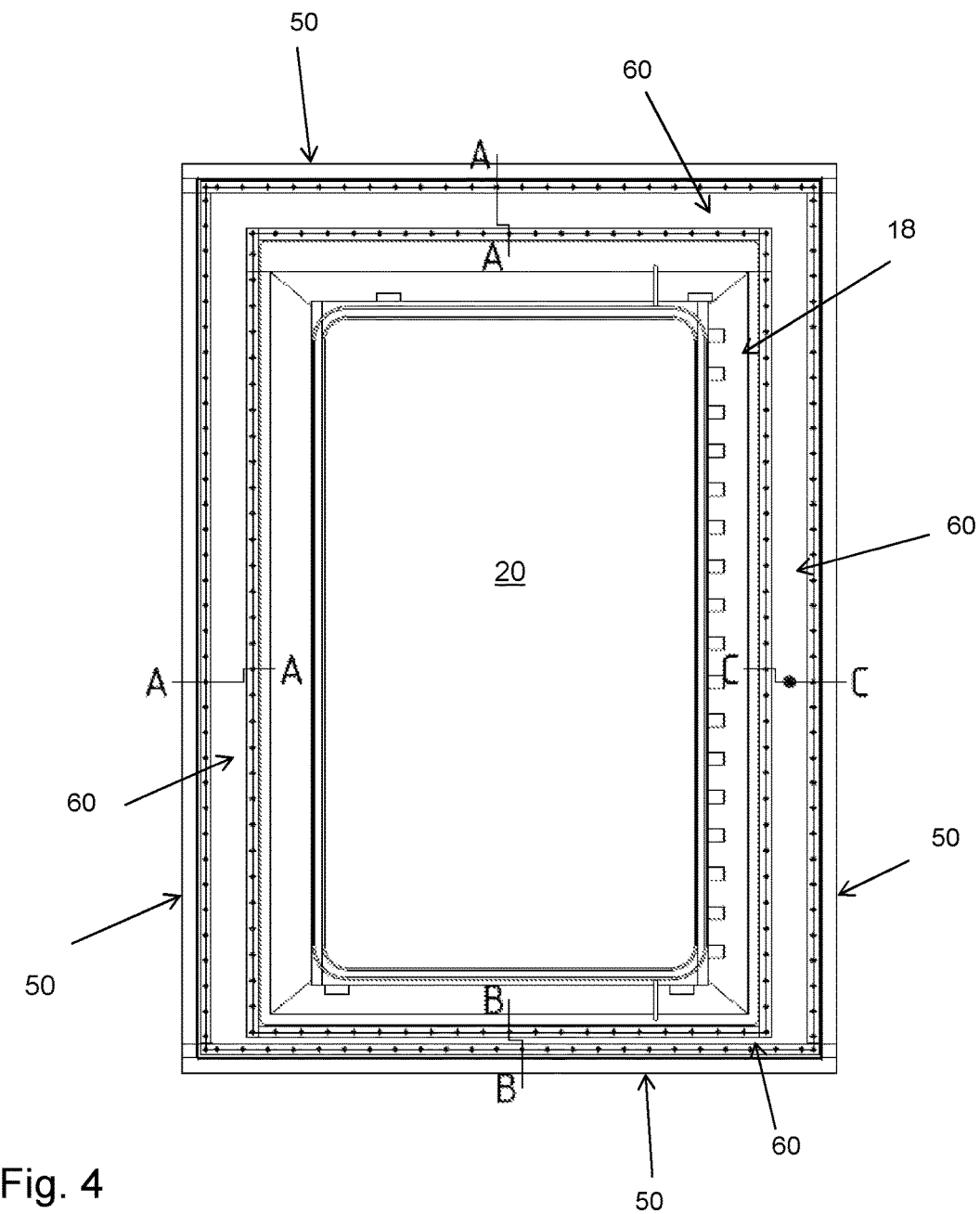
FIG. 4 is a schematic diagram illustrating in front elevation the structure of an example of autoclave.
Figure 5:
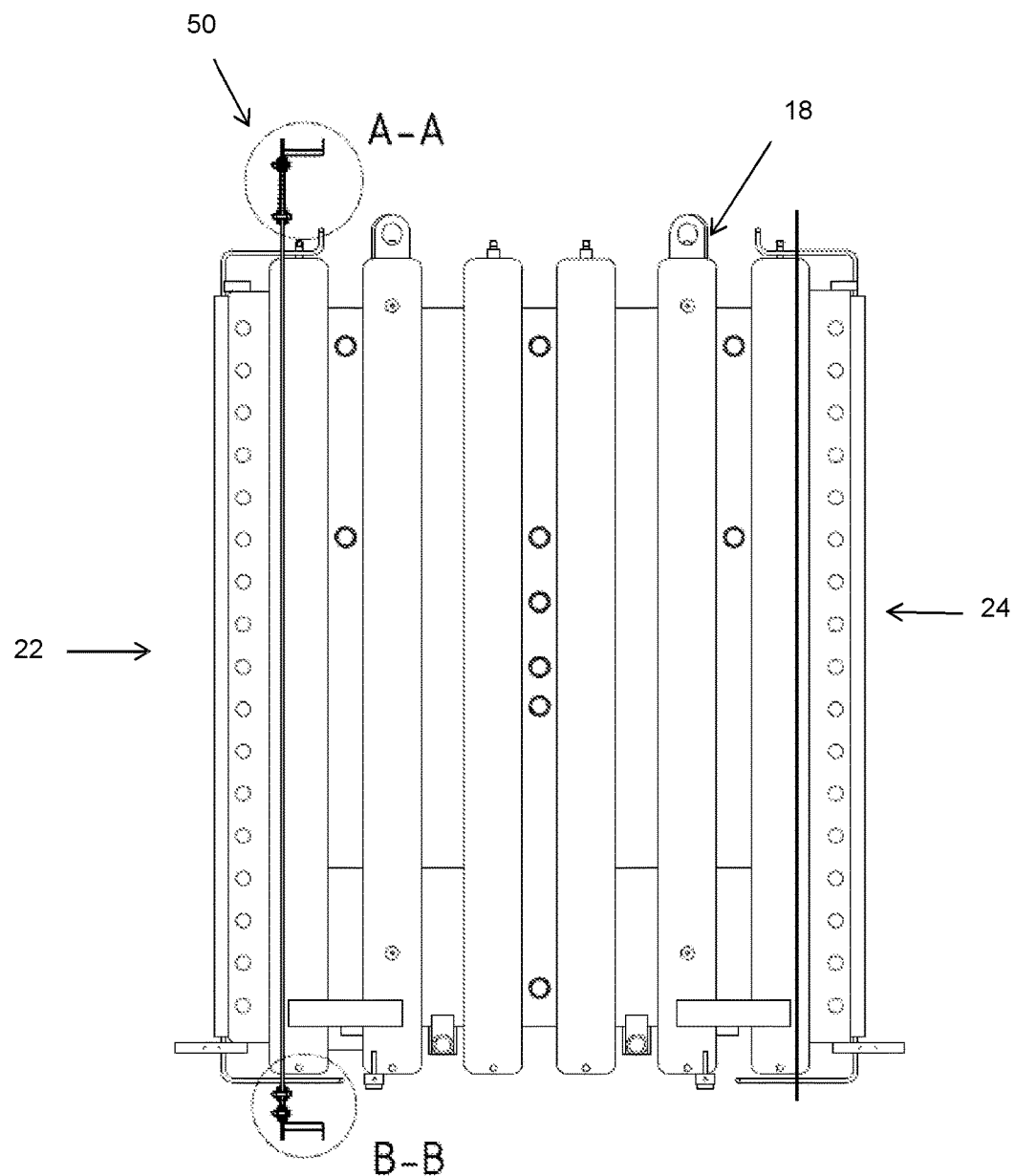
FIG. 5 is a side elevational view of the autoclave of FIG. 4.
Figure 6:
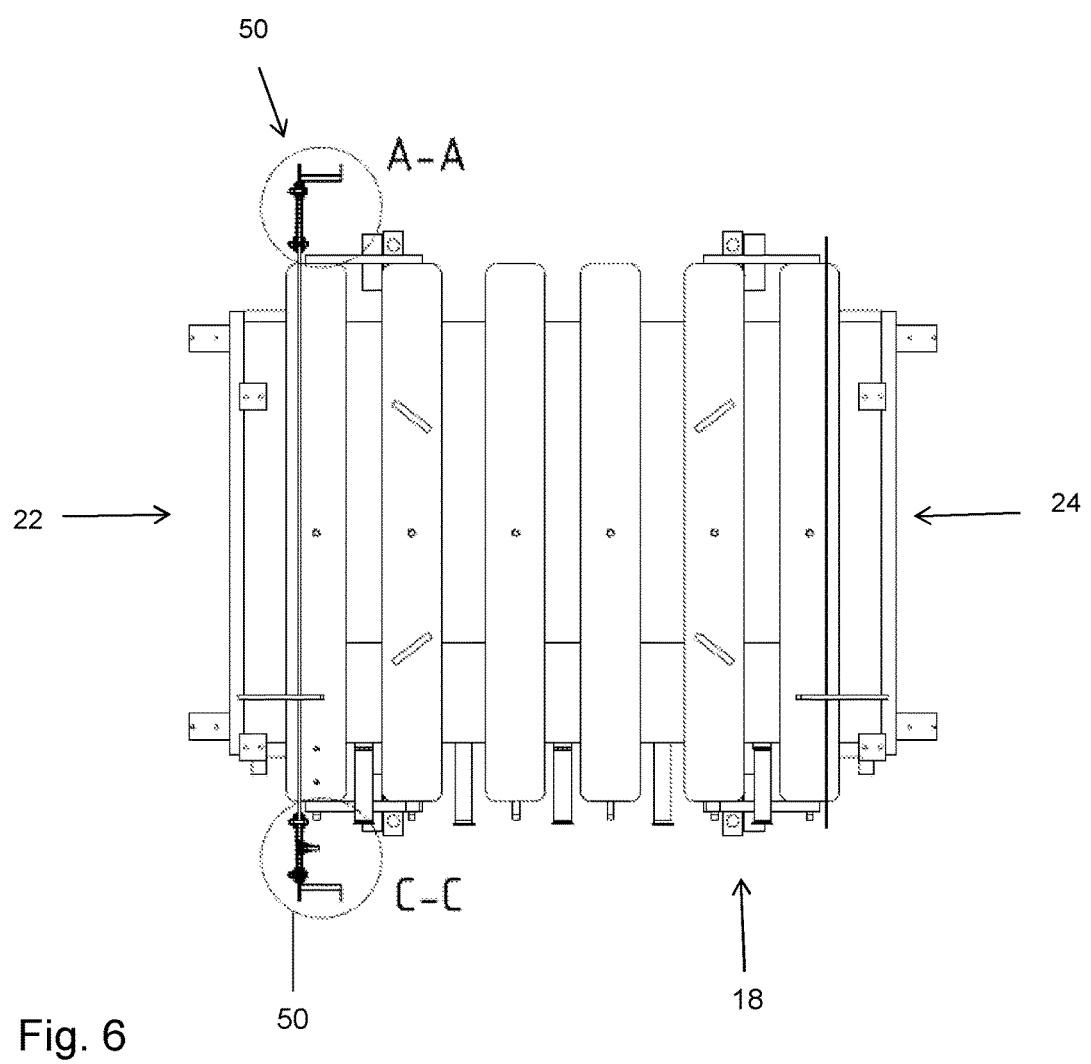
FIG. 6 is a plan view of the autoclave of FIG. 4.

FIG. 4 shows a front elevation view of a sterilization unit 18 having provided therearound a double seal assembly 50 and in particular which extends around the entirety of the perimeter of the sterilization unit 18, that is at each side, at its top and at its bottom. The double seal assembly 50 extends across the side walls, the ceiling or ceiling wall and to the floor surrounding the sterilization unit 18. FIG. 5 shows a side elevation view of the assembly of FIG. 4, whereas FIG. 6 shows a plan view thereof.

The seal chamber 60 is preferably continuous around the whole of the sterilization unit 18, as will be apparent from the view of FIG. 4.

Figure 7:
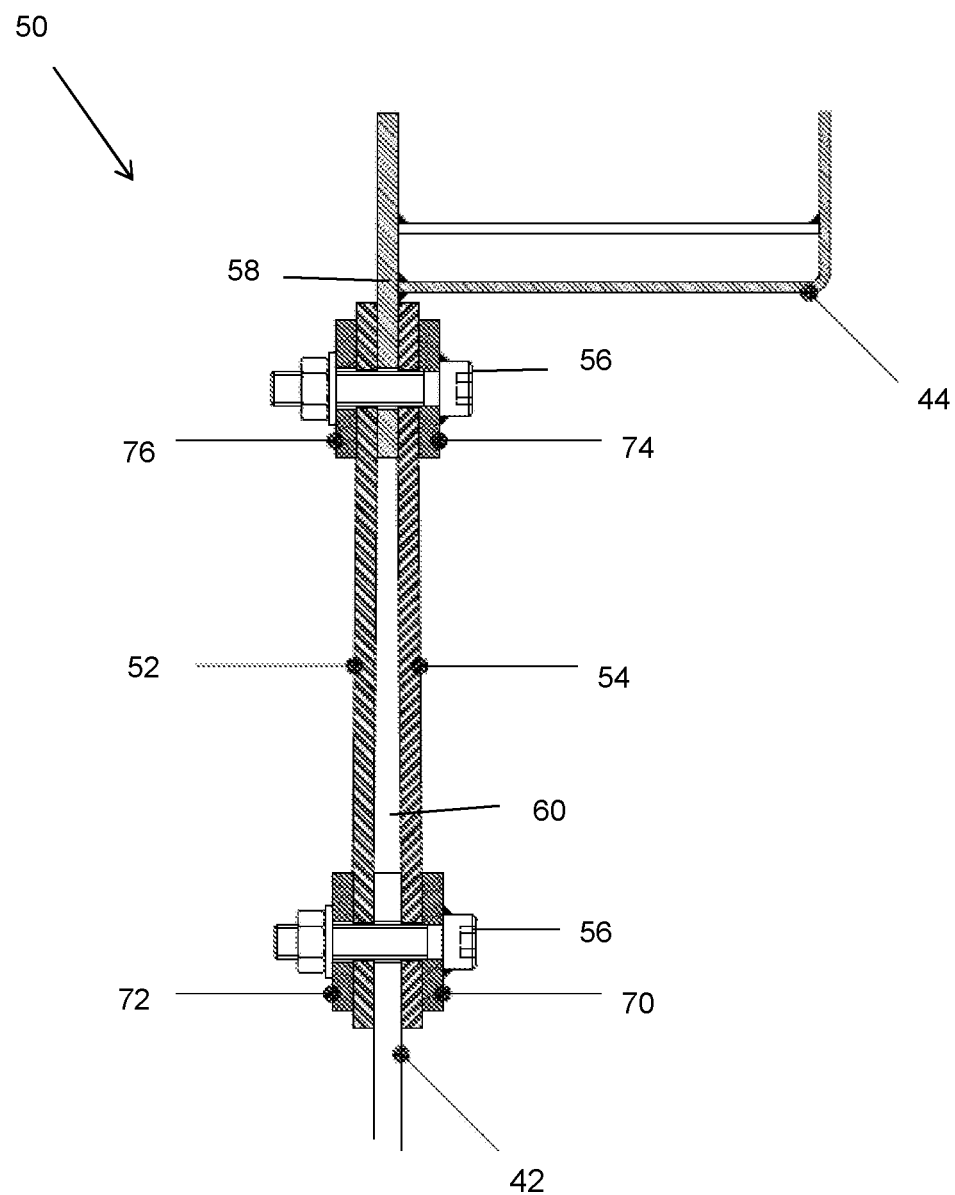
FIG. 7 is a cross-sectional view along lines A-A of FIGS. 5 and 6 showing a preferred embodiment of sealing apparatus.

Referring now to FIG. 7, this shows a cross-sectional view along lines A-A of the double seal assembly 50 of FIG. 4. As can be seen, the structure is as depicted schematically in FIG. 3 and preferably also includes: an inner bolt bar 70, an inner compression bar 72, an outer bolt bar 74 and an outer compression bar 76. These bars 70-76 ensure adequate compression of the seal gaskets 52, 54 when the bolts 56 are tightened.

Figure 8:
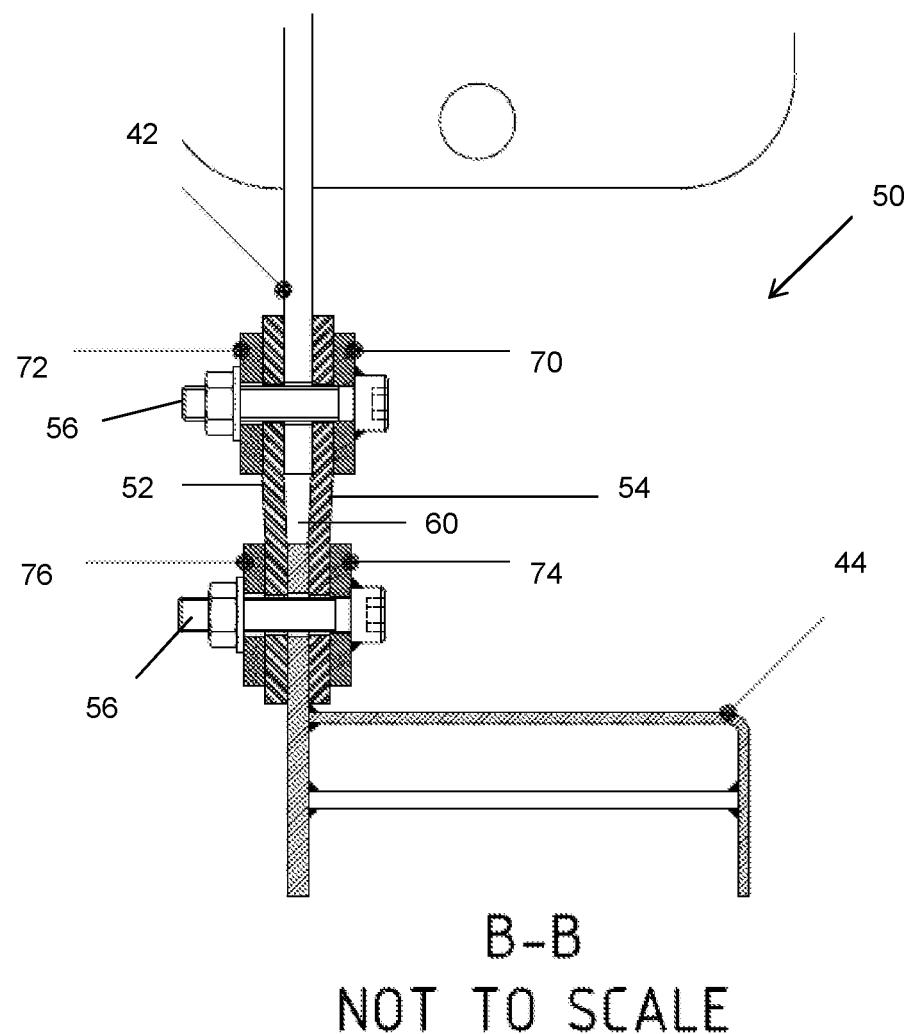
FIG. 8 is a cross-sectional view along lines B-B of FIG. 5 showing another view of the preferred embodiment of sealing apparatus.

FIG. 8 shows a cross-sectional view of the double seal assembly 50 which extends along the bottom of the sterilization unit 18, taken along lines B-B. This is the same as the assembly 50 on the other sides of the sterilization unit 18 save for, in this example, the fact that the spacing between the flange 42 of the sterilization unit 18 and the frame element 44 is less (to provide a lower step into the sterilization chamber 20).

Figure 9:
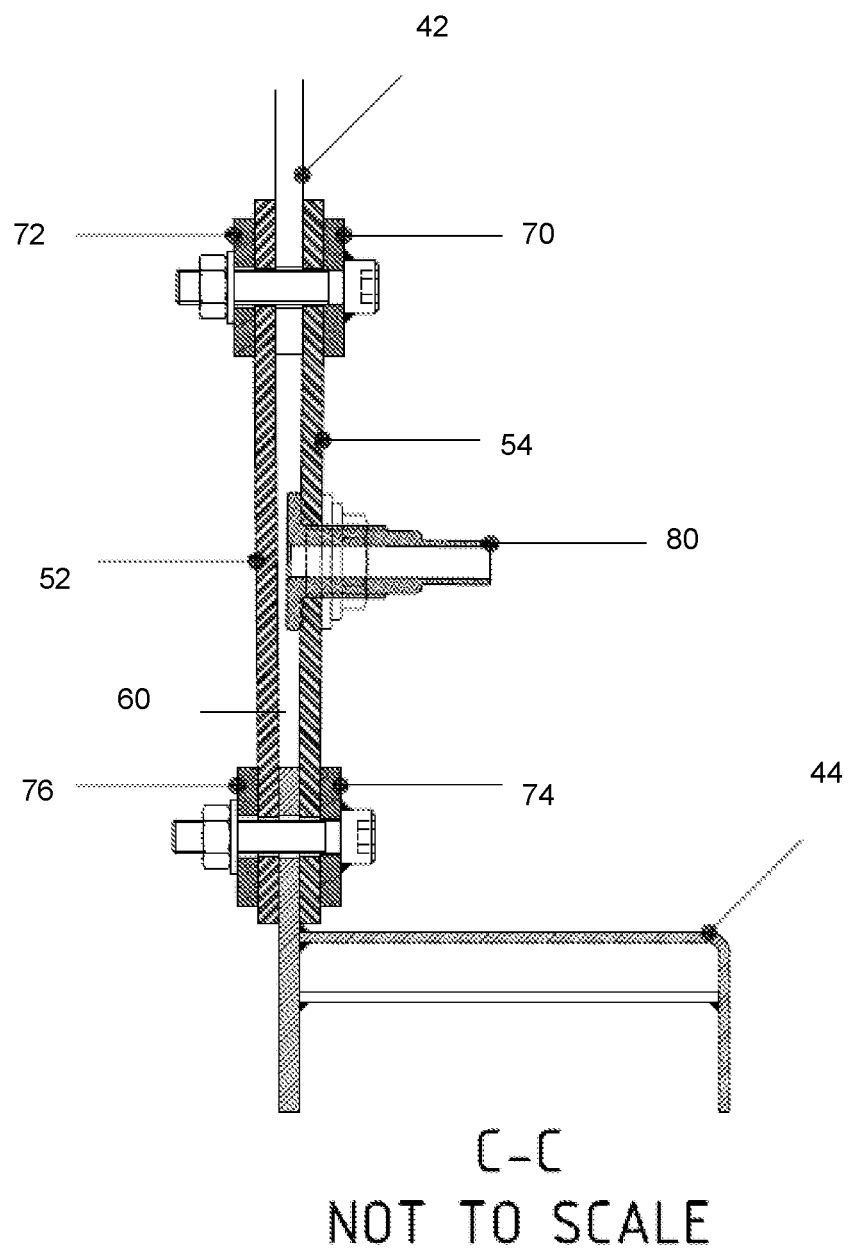
FIG. 9 is a cross-sectional view along lines C-C of FIG. 6 showing another view of the preferred embodiment of sealing apparatus.

Referring now to FIG. 9, this shows a cross-sectional view of the double seal assembly 50 across line C-C of FIG. 4, which is the same as the remainder of the double seal assembly 50, save for the provision of a port 80 within the seal gasket 54 which can be used, in this example, both for filing the space 60 with fluid (or vacuuming the space 50 in the case where this is to be held under vacuum) and for holding a suitable sensor probe, such as the temperature probe 62.

It will be apparent that although in the preferred embodiment the seal chamber 60 extends around the entirety of the perimeter of the sterilization unit 18, such that there is a single seal chamber to monitor, in other embodiments there may be provided a plurality of seal chambers around the perimeter of the sterilization unit 18, each having its own sensor probe and its own port coupling 80. A single seal chamber is preferred as this is continuous around the entirety of the sterilization chamber 18 and does not leave any zones which cannot be monitored.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosure in the abstract accompanying this application is incorporated herein by reference.

The invention claimed is:

1. Apparatus for sealing first and second zones from one another including:
   a sterilization unit disposable in a separating structure between the first and second zones, the sterilization unit including a first chamber and providing therethrough access to the first and second zones;
   a sealing unit disposed around at least a part of the sterilization unit, wherein the sealing unit includes first and second seal elements extending between and providing a seal between the sterilization unit and the separating structure so as to form a second chamber;
   filler material disposed in the second chamber formed between the first and second seal elements, wherein the filler material provides a measurable characteristic; and
   at least one sensor disposed to determine said measurable characteristic.

2. Apparatus according to claim 1, wherein the first and second seal elements are spaced from one another, the filler material being disposed in said space.

3. Apparatus according to claim 1, wherein the filler material is a fluid.

4. Apparatus according to claim 1, wherein the filler material is gaseous.

5. Apparatus according to claim 1, wherein said measurable characteristic is pressure.

6. Apparatus according to claim 1, wherein the filler is of a nature able to escape from either of the seal elements when an incomplete seal between the sterilization unit and the separating structure occurs.

7. Apparatus according to claim 1, including a fitting element attachable to an adjacent structure and providing a support for the first and second seal elements.

8. Apparatus according to claim 1, wherein the sterilization unit includes first and second doors for access through the first chamber thereof.

9. Apparatus according to claim 1, wherein the sterilizer unit is an autoclave and the sealing unit is positioned between an exterior surface of the autoclave and the separating structure so as to form a seal therebetween, wherein the separating structure is a wall.

10. Apparatus according to claim 1, further comprising:
    a flange extending along an exterior surface of the sterilization unit adjoining the separating structure; and
    a frame extending from the separating structure,
    wherein the first and second seal elements extend between the flange and the frame so as to form the second chamber containing the filler material.

11. Apparatus according to claim 10, wherein the sensor is connectable to the second chamber via an opening within the sealing unit.

12. A method of sealing first and second zones from one another including the steps of:
    disposing a sterilization unit between said first and second zones and facing an adjacent structure, the sterilization unit including a first chamber providing therethrough access to the first and second zones;
    disposing a sealing unit around at least a part of the sterilization unit, the sealing unit including first and second seal elements extending between and providing a seal between the sterilization unit and the adjacent structure so as to form a second chamber;
    disposing filler material in the second chamber formed between the first and second seal elements; and
    determining at least one parameter or change in at least one parameter of the filler material over time and therefrom determining the quality of sealing.

13. A method according to claim 12, wherein the first and second seal elements are spaced from one another, the filler material being disposed in said space.

14. A method according to claim 12, wherein the filler material is a fluid.

15. A method according to claim 12, wherein the filler material is gaseous.

16. A method according to claim 12, including disposing at least one sensor to measure said at least one parameter or change in at least one parameter.

17. A method according to claim 12, wherein said method comprises the step of determining the change in at least one parameter and wherein the determined change is a pressure change.

18. A method according to claim 12, wherein the first and second seal elements form the second chamber between an exterior surface of the sterilization unit and the adjacent structure, wherein the method comprises the step of determining the change in the at least one parameter of the filler material comprises coupling a sensor to the second chamber.

19. A method according to claim 18, wherein the step of disposing the filler material comprises pressurizing the second chamber.

20. A method according to claim 18, wherein the sterilization unit is an autoclave and the sealing unit is positioned between an exterior surface of the autoclave and the adjacent structure so as to form a seal therebetween, wherein the adjacent structure is a wall.

\* \* \* \* \*